United States Patent
Lee et al.

(10) Patent No.: US 7,879,998 B2
(45) Date of Patent: Feb. 1, 2011

(54) 4-ALKENYL-2-AZETIDINONE DERIVATIVES, PROCESS FOR PREPARING 4-ALKENYL-2-AZETIDINONE DERIVATIVES AND MULTICYCLIC COMPOUNDS PREPARED USING 4-ALKENYL-2-AZETIDINONE DERIVATIVES

(75) Inventors: Phil Ho Lee, Chuncheon-si (KR); Jungyeon Lee, Chuncheon-si (KR); Seok-Ju Lee, Chuncheon-si (KR)

(73) Assignee: Knu-Industry Cooperation Foundation (KR)

( * ) Notice: Subject to any disclaimer, the term of this patent is extended or adjusted under 35 U.S.C. 154(b) by 796 days.

(21) Appl. No.: 11/765,141

(22) Filed: Jun. 19, 2007

(65) Prior Publication Data

US 2008/0154034 A1    Jun. 26, 2008

(30) Foreign Application Priority Data

Dec. 20, 2006    (KR) .................... 10-2006-0131190

(51) Int. Cl.
C07D 205/08    (2006.01)
C07F 5/00    (2006.01)
(52) U.S. Cl. .......................... 540/200; 556/1
(58) Field of Classification Search .................. 540/200
See application file for complete search history.

(56) References Cited

PUBLICATIONS

Sendo, Chemical & Pharmaceutical Bulletin (1992), 40(9), 2410-18.*
Fugisawa, Chemistry Letters (1995), (11), 1013-14.*
Araki, J. Org. Chem. 1995, 60, 1841-1847.*
Nair, Tetrahedron 60 (2004) 1959-1982.*
Oh, Tetrahedron Letters 44 (2003) 2911-2913.*
"Indium-Mediated Organmetallic Reactions in Aqueous Media: The Nature of the Allylindium Intermediate"; Authors: Chan et al.; J. Am. Chem. Soc. 1999, 121, 3228-3229.
"Enantioselective Total Synthesis of the Fungicide B-Lactam Antibiotic"; Authors: Hoppe, et al.; Tetrahedron 1987, 43, 2467-2474.
Indium-mediated Substitution of 4-Acetoxy-2-azetidinones: Synthesis of 4-Allyl-2-azetidinones; Authors: Kang, et al; Synlett 1999, 4, 447-449.
"B-, y- and -Lactams as conformational constraints in ring-closing metathesis" Authors: Tarling, et al.; J. Chem. Soc., Perkin Trans. 1, 1999, 1695-1701.
"An Efficient Enantioselective Synthesis of the Carbapenam-2-One System. An Approach to (+)- Thienamycin and Related Carbapenems#"; Authors: Meyers, et al.;Tetrahedron Lett. 1987, 28, 5103-5106.
"Metal-Promoted Allylation, Propargylation, or Allenylation of Azetidine-2, 3-diones in Aqueous and Anhydrous Media. Application to the Asymmetric Synthesis of Densely Functionalized 3-Substituted 3-Hydroxy- B-lactams"; Authors: Alcaide, et al.; J. Org. Chem 2001, 15, 5208-5216.
"Metal-Mediated Carbonyl-1, 3-butadien- 2-ylation by 1,4-Bis(methanesulfonyl)-2-butyne or 1,4-Dibromo-2-butyne in Aqueous Media: Asymmetric Synthesis of 3-Substituted 3-Hydroxy-B-lactams"; Authors: Alcaide, et al.;J. Org. Chem 2002, 67, 1925-1928.
"Indium: Inorganic Chemistry"; Author: Dennis G. Tuck; Encyclopedia of Inorganic Chemistry. vol. 3 (CED. R. B. T. King1), 1994, p. 1513-1522.
Thesis of Mr. Seokju Lee of Kang won National University, entitled "In-Meditated Reactions of 1,4-Diabromo-2-butyne or 1,6-Dibromo-2,4-hexadiyne with 4-Acetoxy-2 azetidinones and Its Application" dated Jun. 27, 2006.

* cited by examiner

Primary Examiner—Mark L Berch
(74) Attorney, Agent, or Firm—Cantor Colburn LLP

(57) ABSTRACT

The present invention relates to 4-alkenyl-2-azetidinone derivatives, a process for preparing 4-alkenyl-2-azetidinone derivatives and multicyclic compounds prepared using 4-alkenyl-2-azetidinone derivatives. More specifically, the present invention relates to a 4-alkenyl-2-azetidinone derivative having a novel structure represented by the following chemical formula 1, in which an alkenyl group such as 1,3-dien-2-yl or 1,2,4,5-hexatetraen-3-yl is substituted at the C-4 position of azetidinone; to a process for preparing the 4-alkenyl-2-azetidinone derivative by reacting 4-acetoxy-2-azetidinone with organic indium, which is prepared by reacting a propargyl halide derivative with indium; and to a novel multicyclic compound prepared using the compound represented by the following chemical formula 1 as an intermediate in the Diels-Alder reaction.

[Chemical Formula 1]

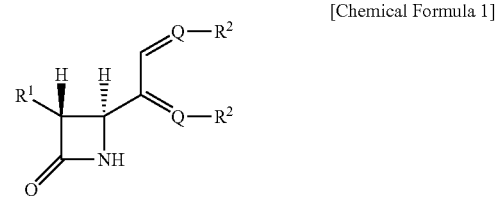

5 Claims, No Drawings

4-ALKENYL-2-AZETIDINONE DERIVATIVES, PROCESS FOR PREPARING 4-ALKENYL-2-AZETIDINONE DERIVATIVES AND MULTICYCLIC COMPOUNDS PREPARED USING 4-ALKENYL-2-AZETIDINONE DERIVATIVES

BACKGROUND OF THE INVENTION

1. Field of the Invention

The present invention relates to 4-alkenyl-2-azetidinone derivatives, a process for preparing 4-alkenyl-2-azetidinone derivatives and multicyclic compounds prepared using 4-alkenyl-2-azetidinone derivatives. More specifically, the present invention relates to a 4-alkenyl-2-azetidinone derivative having a novel structure represented by the following chemical formula 1, in which an alkenyl group such as 1,3-dien-2-yl or 1,2,4,5-hexatetraen-3-Yl is substituted at the C-4 position of azetidinone; to a process for preparing the 4-alkenyl-2-azetidinone derivative by reacting 4-acetoxy-2-azetidinone with organic indium, which is prepared by reacting a propargyl halide derivative with indium; and to a novel multicyclic compound prepared using the compound represented by the following chemical formula 1 as an intermediate in the Diels-Alder reaction.

[Chemical Formula 1]

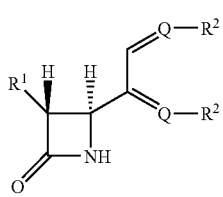

wherein, Q is CH or C=CH; $R^1$: is a hydrogen atom, a hydroxyalkyl group or a protected hydroxyalkyl group having 1 to 6 carbon atoms; and $R^2$ is a hydrogen atom, an alkyl group having 1 to 6 carbon atoms or a phenyl group; provided that, a compound, in which Q is CH, $R^1$ is a protected hydroxyalkyl group and $R^2$ is a hydrogen atom, is excluded.

2. Description of the Related Art

β-lactam is a cyclic amide compound that forms a base skeleton for compounds known as antibiotics such as penicillins and cephalosporins, and it is generally called as "2-azetidinone". Ever since 2-azetidinone derivatives were discovered by L. A. Fleming in 1928, many studies have been conducted. Moreover, 2-azetidinone derivatives are the most frequently used antibiotics as a material for injection and oral administration in the present.

2-Azetidinone derivatives are used widely as β-lactam antibiotics, thus, it is very important to introduce a functional group selectively to a specific position of the compound.

Inherent structural and chemical characteristics of β-lactam have been a matter of concern for organic synthesis researchers in the past. Therefore, many synthetic methods and various β-lactam antibiotic derivatives have been developed. Further, studies on introducing various substituents to β-lactam are being actively conducted at this moment (*Synth. Commun*, 1997, 27, 3083; *Tetrahedron* 1987, 43, 2467; *Synlett* 1999, 4, 447; *J. Chem. Soc., Perkin Trans.* 1, 1999, 1695; *Tetrahedron Lett.* 1987, 28, 5103; *J. Chem. Soc., Perkin Trans.* 1, 1999, 1695; *J. Org. Chem.* 2001, 15, 5208; *J. Org. Chem.* 2001, 15, 5208; *J. Org. Chem.* 2002, 67, 1925; *Encyclopedia of Inorganic Chemistry*. Vol 3 (CED. R. B. T. Kingl), 1994, p. 1513).

However, the 2-azetidinone represented by the chemical formula 1, in which a 1,3-dien-2-yl or 1,2,4,5-hexatetraen-3-yl group is introduced to the C-4 position of β-lactam, is a novel compound that has not been reported in any literature at this point. And, its process for preparation has also not been reported. Furthermore, a process for synthesizing a multicyclic compound by using the compound in the Diels-Alder reaction has not been reported in any literature.

SUMMARY OF THE INVENTION

Therefore, the present invention has been made in view of the above problems, and it is an object of the present invention to provide a 4-alkenyl-2-azetidinone derivative represented by the chemical formula 1 as a novel compound.

It is another object of the present invention to provide a process for preparing the 4-alkenyl-2-azetidinone derivative represented by the chemical formula 1 by reacting 4-acetoxy-2-azetidinone with an organic indium reagent, which is prepared by reacting a propargyl halide derivative with indium.

It is yet another object of the present invention to provide a multicyclic compound prepared by using the 4-alkenyl-2-azetidinone derivative represented by the chemical formula 1 in the Diels-Alder reaction.

In accordance with the present invention, the above and other objects can be accomplished by the provision of a 4-alkenyl-2-azetidinone derivative represented by the following chemical formula 1, a process for preparing the 4-alkenyl-2-azetidinone derivative and a multicyclic compound prepared using 4-alkenyl-2-azetidinone.

[Chemical Formula 1]

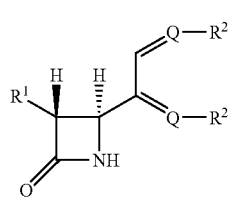

wherein, Q, $R^1$ and $R^2$ are respectively the same as defined in the above.

DESCRIPTION OF THE PREFERRED EMBODIMENTS

The present invention will now be described in greater detail.

According to the present invention, a 4-alkenyl-2-azetidinone derivative represented by the chemical formula 1 is a novel compound which has a structural characteristic in that an alkenyl group such as a diene or a tetraene group is introduced to the C-4 position of β-lactam. The 4-alkenyl-2-azetidinone derivative is also useful as an intermediate for the Diels-Alder reaction in which the diene or the tetraene group of the C-4 position is used.

Substituents of the 4-alkenyl-2-azetidinone derivative will be described in greater detail. "Alkyl groups" or "hydroxyalkyl groups" in the present invention include both straight and branched carbon chains. The "alkyl group" includes both straight and branched carbon chains, and specific examples thereof include methyl, ethyl, propyl, isopropyl, n-butyl, tert-butyl, n-pentyl, isopentyl, n-hexyl, or the like. The "hydroxyalkyl group" is an alkyl group bonded with a hydroxyalkyl group, and a "protected hydroxyalkyl group" is a hydroxyalkyl group bonded with a typical protecting group such as tert-butyldimethylsilyl (TBS), trimethylsilyl (TMS), or triethylsilyl (TES) at the oxygen atom of the hydroxyalkyl group.

A process for preparing the 4-alkenyl-2-azetidinone derivative represented by the chemical formula 1 is included in the scope of the present invention. The preparation process is carried out in the following two steps:

preparing an organic indium reagent represented by the following chemical formula 3 by reacting a propargyl halide derivative represented by the following chemical formula 2 with indium (Step 1):

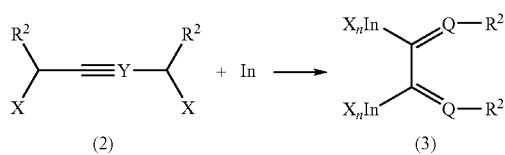

wherein, Q and $R^2$ are respectively the same as defined in the above, X is a halogen atom, Y is —C— or —C—C≡C—, and n is 0 or 2; and preparing the 4-alkenyl-2-azetidinone derivative represented by the following chemical formula 1 by reacting the organic indium reagent represented by the following chemical formula 3 with 4-acetoxy-2-azetidinone represented by the following chemical formula 4 (Step 2):

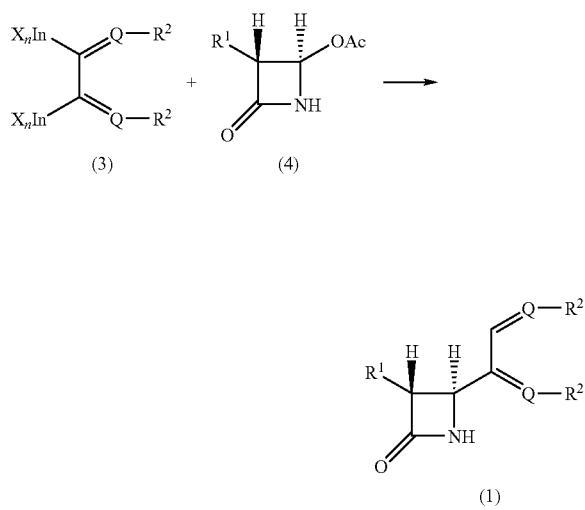

wherein, X, Q, $R^1$, $R^2$, and n are respectively the same as defined in the above.

In the preparation process, the organic indium reagent represented by the chemical formula 3 obtained by reacting the propargyl halide represented by the chemical formula 2 and the indium is used in the subsequent reaction without further carrying out an isolation and purification process. That is, the process is carried out in situ. "In situ" herein refers to a preparation process in which the organic indium represented by the chemical formula 3 obtained by reacting the propargyl derivative represented by the chemical formula 2 with indium in presence of a halide metal salt is used without further carrying out an isolation and purification process. That is, 4-acetoxy-2-azetidinone represented by the chemical formula 4 is added to a reaction solution, and the subsequent reaction is carried out successively. It is more preferable to carry out a reaction in situ when the reaction is used commercially.

The indium is used in the range of 1 to 4 equivalent and preferably 2 to 3 equivalent with respect to the propargyl halide derivative represented by the chemical formula 2.

In the step 1 of preparing the organic indium reagent, a halide metal salt may be used as an additive for reducing the reaction time and improving the yield. The "halide metal salt" used in the reaction is an alkali metal or alkali earth metal halide compound. Specific examples thereof include a compound which forms a bond between a metal selected from lithium (Li), sodium (Na), potassium (K), cesium (Cs), magnesium (Mg), calcium (Ca) or the like and a halogen such as fluoro, chloro, bromo, or iodo. More specific examples of the halide metal salt include lithium chloride, lithium bromide, lithium iodide, potassium iodide, or the like. The halide metal salt is used in the range of 1 to 4 equivalent and preferably 2 to 3 equivalent with respect to 4-acetoxy-2-azetidinone represented by the chemical formula 4.

The reaction solvent used in the preparation process is a typical organic solvent, and the present invention is not particularly limited to the solvent selection. However, it is preferable to use a typical solvent such as dimethylformamide (DMF), tetrahydrofuran (THF), diethylether, dichloromethane, chloroform, or ethylacetate, and more preferably dimethylformamide (DMF) or tetrahydrofuran (THF).

The reaction temperature may be suitably adjusted within the range of room temperature to a reflux temperature of the solvent. It is preferable to carry out the reaction in the range of 15° C. to 120° C., and more preferably 25° C. to 100° C.

The reaction time may be varied depending on the reacting substance, and the type and amount of the solvent. The reaction is terminated when all starting materials are confirmed to be exhausted via TLC or the like. After the reaction is completed, the solvent is evaporated under reduced pressure, and then the product may be isolated and purified via a typical isolation and purification method such as column chromatography.

Meanwhile, the 4-alkenyl-2-azetidinone derivative represented by the chemical formula 1 may be synthesized into multicyclic compounds having various structures by carrying out the Diels-Alder reaction with a dienophile. Therefore, the multicyclic compounds represented by the following novel chemical formula 6a and 6b and a process for preparing thereof using the 4-alkenyl-2-azetidinone derivative represented by the chemical formula 1 are included in the scope of the present invention.

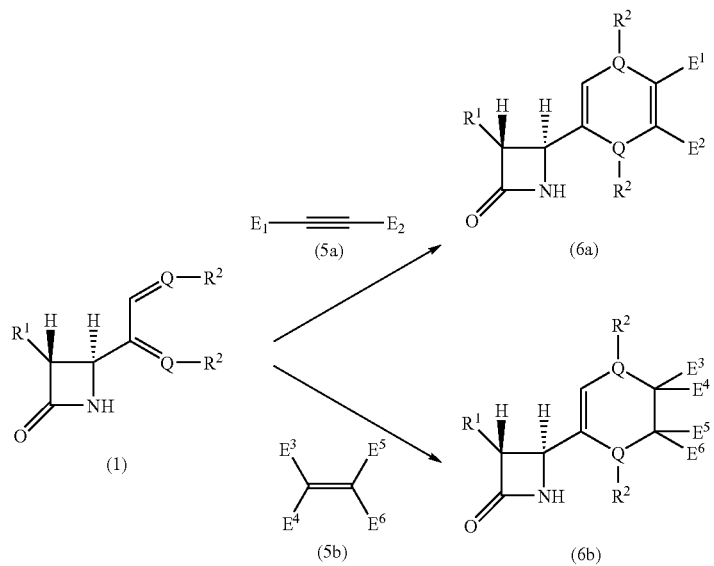

wherein, Q, $R^1$ and $R^2$ are respectively the same as defined in the above, $E^1$, $E^2$, $E^3$, $E^4$, $E^5$ and $E^6$ are respectively a hydrogen atom, a cyano group, C(O)R, C(O)OR or C(O)NR$_2$, provided that R is a hydrogen atom or an alkyl group having 1 to 6 carbon atoms, and $E^3$, $E^4$, $E^5$ and $E^6$ may be bonded with the adjacent group to form a cycle selected from dihydrofuran-2,5-dione, pyrrolidine-2,5-dione, pyrrolidine-2,5-dione substituted with 1-($C_1$-$C_6$ alkyl or phenyl), 2,3-dihydronaphthalene-1,4-dione, and naphthalene-1,4-diol.

The dienophile represented by the chemical formula 5a or 5b, which is used in the Diels-Alder reaction, is a typical compound used generally in this technical field, but the present invention is not limited thereto. Specific examples of the dienophile include maleimide, N-ethylmaleimide, N-phenylmaleimide, dimethyl fumarate, dimethyl maleate, maleic anhydride, tetra(cyano)ethylene, dimethylacetylenedicarboxylate, methyl vinyl ketone, naphtoquinone, ethyl acrylate, ethyl glyoxylate, or the like. The Diels-Alder reaction temperature may be suitably adjusted within the range of room temperature to a reflux temperature of the solvent, and it is preferable to carry out the reaction in the range of 25° C. to 110° C. The reaction time may be varied depending on the reacting substance, and the type and amount of the solvent. The reaction is terminated when all starting materials are confirmed to be exhausted via TLC or the like. After the reaction is completed, the solvent is evaporated under reduced pressure, and then the product may be isolated and purified via a typical isolation and purification method such as column chromatography.

Hereinafter, the present invention will be explained in more detail with reference to the following examples. However, these examples are given for the purpose of illustration and are not to be construed as limiting the scope of the invention.

EXAMPLES

Example 1

Preparation of [3R(1'R,4S)]3-[1'-(tert-butyldimethyl-silyloxy)ethyl]-4-[1",3"-dien]-2"-yl]-2-azetidinone

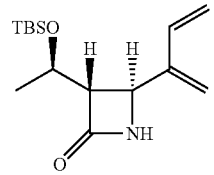

Under nitrogen, indium (172.23 mg, 1.5 mmol) and lithium chloride (174.03 mg, 1.5 mmol) were dissolved in 1.5 ml of a DMF solvent. While stirring the resulting solution, 1,4-dibromo-2-butyne (264.9 mg, 1.25 mmol) was slowly added to the solution. The mixture was stirred for 40 minutes at room temperature, and then [3R(1'R,4S)]-(+)-4-acetoxy-3-[1'(tert-butyldimethylsilyloxy)ethyl]-2-azetidinone (143.72 mg, 0.5 mmol) dissolved in 0.5 ml of DMF was added slowly to the mixture. After stirring the mixture for 3 hours at 90° C., the reaction was terminated by adding a saturated aqueous NH$_4$Cl solution (10 ml) to the mixture. The resulting mixture was extracted using CH$_2$Cl$_2$ (3×20 ml) and washed with a saturated aqueous NaCl solution (20 ml). The extracted organic layer was dried over anhydrous MgSO$_4$, and the residue was filtered off. After removing the solvent from the dried organic layer, column chromatography (eluent: EtOAc/Hexane=1/1) was carried out to isolate the desired product (108 mg, yield: 77%).

$^1$H NMR (400 MHz, CDCl$_3$) δ 6.38 (dd, J=11.12, 17.74 Hz, 1H), 5.84 (s, 1H), 5.46 (d, J=17.72 Hz, 1H), 5.25 (d, J=9.69 Hz, 2H), 5.18 (d, J=11.12 Hz, 1H), 4.48 (d, J=1.40 Hz,

1H), 4.29-4.23 (m, 1H), 2.95 (t, J=5.31 Hz, 1H), 1.22 (d, J=6.40 Hz, 3H), 0.89 (s, 9H), 0.09 (s, 6H)

Example 2

Preparation of 3-[(1',3'-dien)-2'-yl]-2-azetidinone

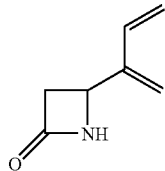

Under nitrogen, indium (172.23 mg, 1.5 mmol) and lithium chloride (174.03 mg, 1.5 mmol) were dissolved in 1.5 ml of a DMF solvent. While stirring the resulting solution, 1,4-dibromo-2-butyne (264.9 mg, 1.25 mmol) was slowly added to the solution. The mixture was stirred for 40 minutes at room temperature, and then 4-acetoxy-2-azetidinone (64.6 mg, 0.5 mmol dissolved in 0.5 ml of DMF was added slowly to the mixture. After stirring the mixture for 3 hours at 90° C., the reaction was terminated by adding a saturated aqueous NH$_4$Cl solution (10 ml) to the mixture. The resulting mixture was extracted using CH$_2$Cl$_2$ (3×20 ml) and washed with a saturated aqueous NaCl solution (20 ml). The extracted organic layer was dried over anhydrous MgSO$_4$, and the residue was filtered off. After removing the solvent from the dried organic layer, column chromatography (eluent: EtOAc/Hexane=1/1) was carried out to isolate the desired product (47 mg, yield: 76%).

$^1$H NMR (400 MHz, CDCl$_3$) δ 6.41 (dd, J=17.94, 11.07 Hz, 1H), 5.99 (s, 1H), 5.26 (s, 1H), 5.20 (s, 1H), 5.16 (dd, J=3.84, 17.81 Hz, 2H), 4.40 (s, 1H), 3.31 (ddd, J=2.41, 5.43, 14.58 Hz, 1H), 2.71 (dd, J=2.63, 14.60 Hz, 1H)

Example 3

Preparation of [3R(1'R,4S)]-3-[(1'-(tert-butyldimethylsilyloxy)ethyl)-4-[(1",2",4",5"-hexatetraen)-3"-yl]-2-azetidinone

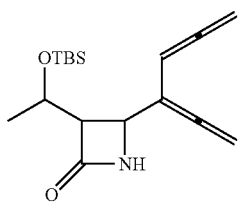

Under nitrogen, indium (172.23 mg, 1.5 mmol) and lithium chloride (174.03 mg, 1.5 mmol) were dissolved in 1.5 ml of a DMF solvent. While stirring the resulting solution, 1,6-dibromo-3,4-hexadiyne (294.88 mg, 1.25 mmol) was slowly added to the solution. The mixture was stirred at room temperature, and then [3R(1'R,4S)]-(+)-4-acetoxy-3-[1'(tert-butyldimethylsilyloxy)ethyl]-2-azetidinone (143.72 mg, 0.5 mmol) dissolved in 0.5 ml of DMF was added slowly to the mixture. After stirring the mixture for 6 hours at room temperature, the reaction was terminated by adding a saturated aqueous NH$_4$Cl solution (10 ml) to the mixture. The resulting mixture was extracted using CH$_2$Cl$_2$ (3×20 ml) and washed with a saturated aqueous NaCl solution (20 ml). The extracted organic layer was dried over anhydrous MgSO$_4$, and the residue was filtered off. After removing the solvent from the dried organic layer, column chromatography (eluent: EtOAc/Hexane=1/1) was carried out to isolate the desired product (96 mg, yield: 77%).

$^1$H NMR (300 MHz, CDCl$_3$) δ 5.96 (s, 1H), 5.79-5.74 (m, 1H), 5.09-5.06 (m, 4H), 4.33 (d, J=2.01 Hz, 1H), 4.28-4.20 (m, 1H), 3.19-3.17 (m, 1H), 1.19 (d, J=6.31 Hz), 0.87 (s, 9H), 0.07 (s, 6H)

Example 4

Preparation of 4-[(1'2'4'5'-hexatetraen)-3'-yl]-2-azetidinone

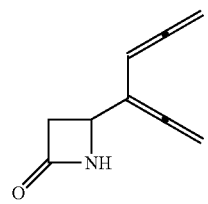

Under nitrogen, indium (172.23 mg, 1.5 mmol) and lithium chloride (174.03 mg, 1.5 mmol) were dissolved in 1.5 ml of a DMF solvent. While stirring the resulting solution, 1,6-dibromo-3,4-hexadiyne (294.88 mg, 1.25 mmol) was slowly added to the solution. The mixture was stirred at room temperature, and then 4-acetoxy-2-azetidinone (64.6 mg, 0.5 mmol dissolved in 0.5 ml of DMF was added slowly to the mixture. After stirring the mixture for 6 hours at room temperature, the reaction was terminated by adding a saturated aqueous NH$_4$Cl solution (10 ml) to the mixture. The resulting mixture was extracted using CH$_2$Cl$_2$ (3×20 ml) and washed with a saturated aqueous NaCl solution (20 ml). The extracted organic layer was dried over anhydrous MgSO$_4$, and the residue was filtered off. After removing the solvent from the dried organic layer, column chromatography (eluent: EtOAc/Hexane=1/1) was carried out to isolate the desired product (33 mg, yield: 45%).

$^1$H NMR (300 MHz, CDCl$_3$) δ 5.95 (s, 1H), 5.80 (t, J=6.70 Hz, 1H), 5.12 (q, J=6.11 Hz, 2H), 4.22 (m, 1H), 3.20 (ddd, J=1.68, 5.09, 14.78 Hz, 1H), 2.90 (dt, J=2.03, 14.79 Hz, 1H)

Example 5

Preparation of [3R(1'R,4S)]-3-[(1'-(tert-butyldimethylsilyloxy)ethyl)-4-](4",4",5",55"-tetracyano-1-cyclohexyl)-2-azetidinone

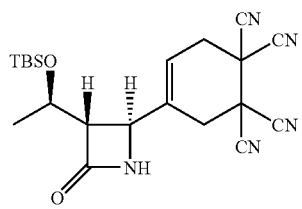

In a V-VIAL® vial, [3R(1'R,4S)]-3-[(1'-tert-butyldimethylsilyloxy)ethyl]-4[1",3"-dien]-2"-yl]-2-azetidinone (140.74 mg, 0.5 mmol) and tetracyano ethylene (128.09 mg, 1.0 mmol) were dissolved in 0.8 ml of a benzene solvent. The resulting solution was stirred for 5 hours at room temperature.

Then, the reaction was terminated by adding a saturated aqueous NH$_4$Cl solution (10 ml) to the solution. The mixture was extracted using CH$_2$Cl$_2$ (3×20ml) and washed with a saturated aqueous NaCl solution (20 ml). The extracted organic layer was dried over anhydrous MgSO$_4$, and the residue was filtered off. After removing the solvent from the dried organic layer, column chromatography (eluent: EtOAc/Hexane =1/1) was carried out to isolate the desired product (175.6 mg, yield: 86%).

$^1$H NMR (400 MHz, CDCl$_3$) δ 8.23 (s, 1H), 5.83 (s, 1H), 4.08 (t, J=5.41 Hz, 1H), 4.00 (s, 1H), 3.51 (s, 1H), 3.45 (s, 1H), 3.34 (d, J=10.22 Hz, 1H), 3.14 (d, J=18.65 Hz, 1H), 2.83 (dd, J=2.31, 2.31 Hz, 1H), 1.10 (d, J=6.22 Hz, 3H), 0.79 (s, 9H), 0.01 (s, 6H)

Example 6

Preparation of [3R(1'R,4S)]-3-[(1'-(tert-butyldimethylsilyloxy)ethyl)-4-[(4'',5''-dimethoxycarbonyl-1'', 4''-cyclohexadienyl]-2-azetidinone

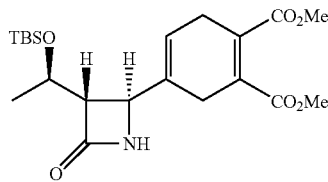

In a V VIAL® vial, [3R(1'R,4S)]-3-[(1'-tert-butyldimethylsilyloxy)ethyl]-4-[(1'', 3''-dien)-2''-yl]-2-azetidinone (140.74 mg, 0.5 mmol) and dimethylacetylenedicarboxylate (98.06 mg, 1.0 mmol) were dissolved in 0.8 ml of a benzene solvent. The resulting solution was stirred for 48 hours at 83° C. Then, the reaction was terminated by adding a saturated aqueous NH$_4$Cl solution (10 ml) to the solution. The mixture was extracted using CH$_2$Cl$_2$ (3 ×20 ml) and washed with a saturated aqueous NaCl solution (20 ml). The extracted organic layer was dried over anhydrous MgSO$_4$, and the residue was filtered off. After removing the solvent from the dried organic layer, column chromatography (eluent: EtOAc/Hexane =1/3) was carried out to isolate the desired product (175.7 mg, yield: 83%).

$^1$H NMR (400 MHz, CDCl$_3$) δ 6.00 (s, 1H), 5.76 (s, 1H), 4.20 (t, J=5.78 Hz, 1H), 4.13 (s, 1H), 3.79 (s, 6H), 3.09-3.05 (m, 3H), 2.99-2.94 (m, 1H), 2.89 (dd, J=1.98, 2.13 Hz, 1H), 1.24 (d, J=6.27 Hz, 3H), 0.88 (s, 9H), 0.09 (s, 1H)

Example 7

Preparation of [3R(1'R,4S)]-3-[(1'-(tert-butyldimethylsilyloxy)ethyl)-4-](9'',10''-dihydroxy-1'',4''-dihydroanthracen-2''-yl)-azetidin-2-one

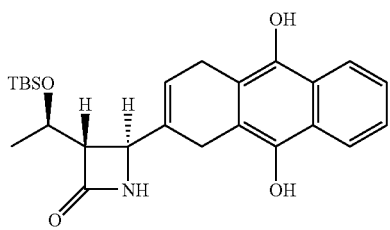

In a V-VIAL® vial, [3R(1'R,4S)]-3-[(1'-tert-butyldimethylsilyloxy)ethyl]-4-[(1'',3''-dien)-2''-yl]-2-azetidinone (140.74 mg, 0.5 mmol) and 1,4-naphtoquinone (158.15 mg, 1.0 mmol) were dissolved in 0.8 ml of a benzene solvent. The resulting solution was stirred for 48 hours at 83° C. Then, the reaction was terminated by adding a saturated aqueous NH$_4$Cl solution (10 ml) to the solution. The mixture was extracted using CH$_2$Cl$_2$ (3×20 ml) and washed with a saturated aqueous NaCl solution (20 ml). The extracted organic layer was dried over anhydrous MgSO$_4$, and the residue was filtered off. After removing the solvent from the dried organic layer, column chromatography (eluent: EtOAc/Hexane =1/3) was carried out to isolate the desired product (184.7 mg, yield: 84%).

$^1$H NMR (400 MHz, CDCl$_3$) δ 8.12-8.09 (m, 2H), 7.74-7.71 (m, 2H), 5.93 (s, 1H), 5.86 (s, 1H), 4.27 (d, J=5.65 Hz, 2H), 3.32-3.29 (m, 2H), 3.26-3.23 (m, 2H), 2.97 (s, 1H), 1.28(d, J=6.13 Hz, 3H), 0.91 (s, 9H), 0.12 (d, J=4.67 Hz, 6H)

Example 8

Preparation of [3R(1'R,4S)]-3-[(1'-(tert-butyldimethylsilyloxy)ethyl)-4-](4'',5''-dimethoxycarbonyl-1''-cyclohexenyl)-2-azetidinone

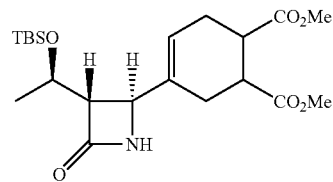

In a V-VIAL® vial, [3R(1'R,4S)]-3-[(1'-tert-butyldimethylsilyloxy)ethyl]-4-[(1'',3''-dien)-2''-yl]-2-azetidinone (140.74 mg, 0.5 mmol) and dimethyl maleate(144.13 mg, 1.0 mmol) were dissolved in 0.8 ml of a benzene solvent. The resulting solution was stirred for 48 hours at 83° C. Then, the reaction was terminated by adding a saturated aqueous NH$_4$Cl solution (10 ml) to the solution. The mixture was extracted using CH$_2$Cl$_2$ (3×20 ml) and washed with a saturated aqueous NaCl solution (20 ml). The extracted organic layer was dried over anhydrous MgSO$_4$, and the residue was filtered off. After removing the solvent from the dried organic layer, column chromatography (eluent: EtOAc/Hexane =1/3) was carried out to isolate the desired product (204.3 mg, yield: 96%).

$^1$H NMR (400 MHz, CDCl$_3$) Isomer A δ 6.07 (s, 1H), 5.73 (d, J=5.16 Hz, 1H), 4.21-4.15 (m, 1H), 3.70 (s, 6H), 2.91-2.84 (m, 2H), 2.49 (t, J=16.46 Hz, 2H), 2.26-2.17 (m, 2H), 1.23 (dd, J=6.09, 6.24 Hz, 3H), 0.88 (s, 9H), 0.08 (s, 6H); Isomer B δ 6.10 (s, 2H), 5.73 (d, J=5.16 Hz, 1H), 4.21-4.15 (m, 1H), 3.70 (s, 6H), 2.91-2.84 (m, 2H), 2.49 (t, J=16.46 Hz, 2H), 2.26-2.17 (m, 2H), 1.23 (dd, J=6.09, 6.24 Hz, 3H), 0.88 (s, 9H), 0.08 (s, 6H)

Example 9

Preparation of 5-3-[(1-(tert-butyldimethylsilyloxy)ethyl]-4-oxoazetidin-2-yl]-3a,4,7,7a-tetrahydroisoindole-1,3-dione

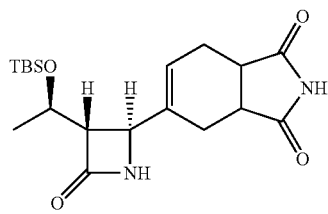

In a V VIAL® vial, [3R(1'R,4S)]-3-[(1'-tert-butyldimethylsilyloxy)ethyl]-4-[(1",3"-dien)-2"-yl]-2-azetidinone (140.74 mg, 0.5 mmol) and maleimide (97.07 mg, 1.0 mmol) were dissolved in 0.8 ml of a benzene solvent. The resulting solution was stirred for 24 hours at 83° C. Then, the reaction was terminated by adding a saturated aqueous NH$_4$Cl solution (10 ml) to the solution. The mixture was extracted using CH$_2$Cl$_2$ (3×20 ml) and washed with a saturated aqueous NaCl solution (20 ml). The extracted organic layer was dried over anhydrous MgSO$_4$, and the residue was filtered off. After removing the solvent from the dried organic layer, column chromatography (eluent: EtOAc/Hexane =1/3) was carried out to isolate the desired product (184.7 mg, yield: 99%).

$^1$H NMR (400 MHz, CDCl$_3$) δ Isomer A 7.85 (s, 1H), 5.95-5.91 (m, 1H), 5.80 (s, 1H), 4.25-4.17 (m, 2H), 3.21-3.15 (m, 2H), 2.70-2.65 (m, 2H), 1.14 (d, J=6.24 Hz, 3H), 0.87 (s, 9H), 0.08 (s, 6H); Isomer B 7.97 (s, 1H), 5.95-5.91 (m, 1H), 5.84 (s, 1H), 4.25-4.17 (m, 2H), 3.27-3.20 (m, 2H), 2.77-2.72 (m, 2H), 1.23 (d, J=6.21 Hz, 3H), 0.87 (s, 9H), 0.08 (s, 6H)

Example 10

Preparation of 5-3-[(1-(tert-butyldimethylsilyloxy)ethyl]-4-oxoazetidin-2-yl-2-ethyl]-3a,4,7,7a-tetrahydroisoindole-1,3-dione

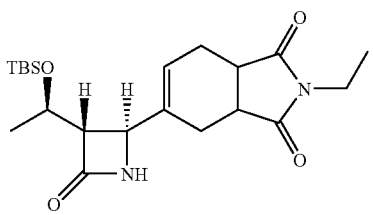

In a V VIAL® vial, [3R(1'R,4S)]-3-[(1'-tert-butyldimethylsilyloxy)ethyl]-4-[(1",3"-dien)-2"-yl]-2-azetidinone (56.3 mg, 0.2 mmol), N-ethylmaleimide (50 mg, 0.4 mmol) and indium trichloride (1.9 mg, 0.01 mmol) were dissolved in 0.3 ml of a CH$_3$CN solvent. The resulting solution was stirred for 24 hours at room temperature. Then, the reaction was terminated by adding a saturated aqueous NH$_4$Cl solution (10 ml) to the solution. The mixture was extracted using CH$_2$Cl$_2$ (3×20 ml) and washed with a saturated aqueous NaCl solution (20 ml). The extracted organic layer was dried over anhydrous MgSO$_4$, and the residue was filtered off. After removing the solvent from the dried organic layer, column chromatography (eluent: EtOAc/Hexane =1/3) was carried out to isolate the desired product (75.6 mg, yield: 93%).

$^1$H NMR (400 MHz, CDCl$_3$) δ 5.88 (d, J=12.03 Hz, 2H), 4.24-4.15 (m, 1H), 4.11 (s, 1H), 3.49 (dd, J=7.16, 7.05 Hz, 2H), 3.16-3.07 (m, 3H), 2.24-2.08 (m, 2H), 1.25 (d, J=6.30, 3 h), 1.09 (t, J=3.78, 7.16 Hz, 3H), 0.87 (s, 9H), 0.08 (d, J=3.84 Hz, 6H)

Example 11

Preparation of 5-3-[(1-(tert-butyldimethylsilyloxy)ethyl]-4-oxoazetidin-2-yl-2-phenyl]-3a,4,7,7a-tetrahydroisoindole-1,3-dione

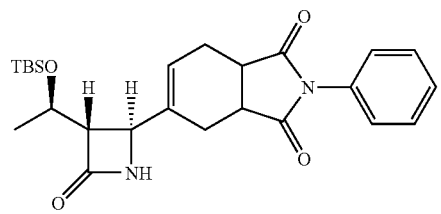

In a V VIAL® vial, [3R(1'R,4S)]-3-[(1'-tert-butyldimethylsilyloxy)ethyl]-4-[(1",3"-dien)-2"-yl]-2-azetidinone (56.3 mg, 0.2 mmol), N-phenylmaleimide (69.3 mg, 0.4 mmol) and indium trichloride (1.9 mg, 0.01 mmol) were dissolved in 0.3 ml of a CH$_3$CN solvent. The resulting solution was stirred for 48 hours at room temperature. Then, the reaction was terminated by adding a saturated aqueous NH$_4$Cl solution (10 ml) to the solution. The mixture was extracted using CH$_2$Cl$_2$ (3×20 ml) and washed with a saturated aqueous NaCl solution (20 ml). The extracted organic layer was dried over anhydrous MgSO$_4$, and the residue was filtered off. After removing the solvent from the dried organic layer, column chromatography (eluent: EtOAc/Hexane =1/3) was carried out to isolate the desired product (90.9 mg, yield: 100%)

$^1$H NMR (400 MHz, CDCl$_3$) δ 7.47 (t, J=7.62 Hz, 2H), 7.39 (t, J=7.12 Hz, 1H), 7.19 (d, J=7.73 Hz, 2H), 5.97 (t, J=3.24 Hz, 1H), 5.58 (s, 1H), 4.21 (t, J=8.06 Hz, 2H), 3.38-3.27 (m, 2H), 2.87-2.75 (m, 3H), 2.38-2.25 (m, 2H), 1.24 (d, J=3.12 Hz), 0.88 (s, 9H), 0.73 (s, 6H)

Example 12

Preparation of [3R(1'R,4S)]-3-[(1'-(tert-butyldimethylsilyloxy)ethyl)-4-[(4"-acetyl-1"-cyclohexenyl)-2-azetidinone

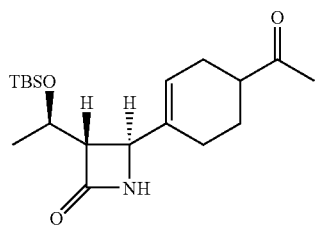

In a V VIAL® vial, [3R(1'R,4S)]-3-[(1'-tert-butyldimethylsilyloxy)ethyl]-4-[(1",3"-dien)-2"-yl]-2-azetidinone (140.74 mg, 0.5 mmol) and methyl vinyl ketone (70.09 mg, 1.0 mmol) were dissolved in 0.8 ml of a benzene solvent. The resulting solution was stirred for 48 hours at 83° C. Then, the reaction was terminated by adding a saturated aqueous NH₄Cl solution (10 ml) to the solution. The mixture was extracted using CH₂Cl₂ (3×20 ml) and washed with a saturated aqueous NaCl solution (20 ml). The extracted organic layer was dried over anhydrous MgSO₄, and the residue was filtered off. After removing the solvent from the dried organic layer, column chromatography (eluent: EtOAc/Hexane =1/1) was carried out to isolate the desired product (100.2 mg, yield: 57%).

¹H NMR (400 MHz, CDCl₃) Isomer A δ 6.10 (s, 1H), 5.75-5.73 (m, 1H), 4.2-4.16 (m, 1H), 4.09-4.07 (m, 1H), 2.86 (dd, J=2.07, 4.96 Hz, 1H), 2.60-2.57 (m, 1H), 2.23-2.21 (m, 2H), 2.20-2.18 (m, 3H), 2.09-2.08 (m, 1H), 2.06-2.00 (m, 2H), 1.26 (d, J=7.14 Hz, 1H), 1.23 (dd, J=6.17, 6.17 Hz, 3H), 0.9 (s, 9H), 0.08 (s, 6H); Isomer B δ 6.07 (s, 1H), 5.75-5.73 (m, 1H), 4.2-4.16 (m, 1H), 4.09-4.07 (m, 1H), 2.81 (dd, J=2.14, 4.42 Hz, 1H), 2.60-2.57 (m, 1H), 2.23-2.21 (m, 2H), 2.20-2.18 (m, 3H), 2.09-2.08 (m, 1H), 2.06-2.00 (m, 2H), 1.26 (d, J=7.14 Hz, 1H), 1.23 (dd, J=6.17, 6.17 Hz, 3H), 0.9 (s, 9H), 0.08 (s, 6H)

Example 13

Preparation of [3R(1'R,4S)]-3-[(1'-(tert-butyldimethylsilyloxy)ethyl)-4-[(4"ethoxycarbonyl-1"-cyclohexenyl]-2-azetidinone

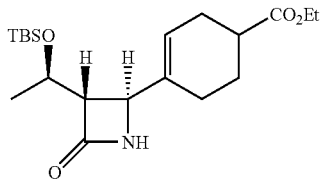

In a V-VIAL® vial, [3R(1'R,4S)]-3-[(1'-tert-butyldimethylsilyloxy)ethyl]-4-[(1",3"-dien)-2"-yl]-2-azetidinone (140.74 mg, 0.5 mmol) and ethyl acrylate (100.12 mg, 1.0 mmol) were dissolved in 0.8 ml of a benzene solvent. The resulting solution was stirred for 48 hours at 83° C. Then, the reaction was terminated by adding a saturated aqueous NH₄Cl solution (10 ml) to the solution. The mixture was extracted using CH₂Cl₂ (3 ×20 ml) and washed with a saturated aqueous NaCl solution (20 ml). The extracted organic layer was dried over anhydrous MgSO₄, and the residue was filtered off. After removing the solvent from the dried organic layer, column chromatography (eluent: EtOAc/Hexane =1/1) was carried out to isolate the desired product (146.9 mg, yield: 77%).

¹H NMR (400 MHz, CDCl₃) Isomer A δ5.86 (s, 1H), 5.74-5.71 (m, 1H), 4.22-4.08 (m, 4H), 2.86 (dd, J=2.00, 4.87 Hz, 1H), 2.55-2.49 (m, 1H), 2.33-2.30 (m, 2H), 2.22-2.14 (m, 1H), 2.07-1.07 (m, 2H), 1.77-1.66 (m, 1H), 1.28-1.21 (m, 6H), 0.87 (s, 9H), 0.08 (s, 6H); Isomer B δ 5.84 (s, 1H), 5.74-5.71 (m, 1H), 4.22-4.08 (m, 4H), 2.82 (dd, J=2.12, 4.27 Hz, 1H), 2.55-2.49 (m, 1H), 2.33-2.30 (m, 2H), 2.22-2.14 (m, 1H), 2.07-1.07 (m, 2H), 1.77-1.66 (m, 1H), 1.28-1.21 (m, 6H), 0.87 (s, 9H), 0.08 (s, 6H)

Example 14

Preparation of 5-(4-oxoazetidin-2-yl)-3a,4,7,7a-tetrahydroisoindole-1,3-dione

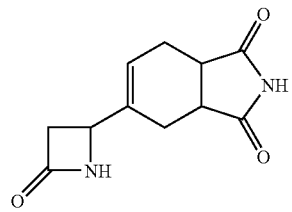

In a V-VIAL® vial, 3-[(1',3'-dien)-2'-yl]-2-azetidinone (36.9 mg, 0.3 mmol), maleimide (58.24 mg, 0.6 mmol) and indium trichloride (2.78 mg, 0.015 mmol) were dissolved in 0.5 ml of a CH₃CN solvent. The resulting solution was stirred for 24 hours at room temperature. Then, the reaction was terminated by adding a saturated aqueous NH₄Cl solution (10 ml) to the solution. The mixture was extracted using CH₂Cl₂ (3 ×20 ml) and washed with a saturated aqueous NaCl solution (20 ml). The extracted organic layer was dried over anhydrous MgSO₄, and the residue was filtered off. After removing the solvent from the dried organic layer, column chromatography (eluent: EtOAc/Hexane =1/1) was carried out to isolate the desired product (47.4 mg, yield: 72%).

¹H NMR (400 MHz, CDCl₃) δ 12.88 (s, 1H), 8.06 (s, 1H), 5.81 (t, J=3.27 Hz, 1H), 3.50 (d, J=1.49 Hz, 1H), 3.17 (d, J=6.73 Hz, 1H), 3.11 (d, J=7.52 Hz, 1H), 2.99 (dd, J=5.29, 14.58 Hz, 1H), 2.43 (d, J=14.01 Hz, 1H), 2.37-2.28 (m, 2H), 2.15 (dd, J=7.51, 14.90 Hz, 1H), 2.06 (dd, J=7.04, 15.10 Hz,1H)

Example 15

Preparation of 5-(4-oxoazetidin-2-yl)-2-phenyl-3a,4,7,7a-tetrahydroisoindole-1,3-dione

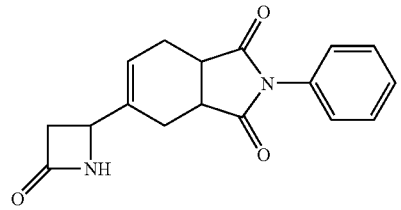

In a V-VIAL® vial, 3-[(1',3'-dien)-2'-yl]-2-azetidinone (36.9 mg, 0.3 mmol), N-phenylmaleimide (103.9 mg, 0.6 mmol) and indium trichloride (2.78 mg, 0.015 mmol) were dissolved in 0.5 ml of a CH₃CN solvent. The resulting solution was stirred for 24 hours at room temperature. Then, the reaction was terminated by adding a saturated aqueous NH₄Cl solution (10 ml) to the solution. The mixture was extracted using CH₂Cl₂ (3 ×20 ml) and washed with a saturated aqueous NaCl solution (20 ml). The extracted organic layer was dried over anhydrous MgSO₄, and the residue was filtered off. After removing the solvent from the dried organic layer, column chromatography (eluent: EtOAc) was carried out to isolate the desired product (88.9 mg, yield: 100%).

¹H NMR (400 MHz, CDCl₃) δ 7.48-7.43 (m, 2H), 7.40-7.37 (m, 1H), 7.19 (d, J=8.04 Hz, 2H), 5.97 (dd, J=3.26, 6.54

Hz, 1H), 5.81 (d, J=16.70 Hz, 1H), 4.14 (s, 1H), 3.39-3.28 (m, 2H), 3.20-3.08 (m, 2H), 2.83-2.73 (m, 1H), 2.63-2.58 (m, 1H), 2.38-2.32 (m, 1H), 2.29-2.23 (m, 1H)

Example 16

Preparation of 4-(4',5'-dimethoxycarbonyl-1'-cyclohexenyl)-2-azetidinone

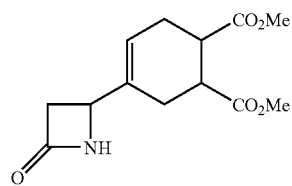

In a V-VIAL® vial, 3-[(1',3'-dien)-2'-yl]-2-azetidinone (36.9 mg, 0.3 mmol), dimethyl maleate (86.48 mg, 0.6 mmol) and indium trichloride (2.78 mg, 0.015 mmol) were dissolved in 0.5 ml of a $CH_3CN$ solvent. The resulting solution was stirred for 24 hours at room temperature. Then, the reaction was terminated by adding a saturated aqueous $NH_4Cl$ solution (10 ml) to the solution. The mixture was extracted using $CH_2Cl_2$ (3 ×20 ml) and washed with a saturated aqueous NaCl solution (20 ml). The extracted organic layer was dried over anhydrous $MgSO_4$, and the residue was filtered off. After removing the solvent from the dried organic layer, column chromatography (eluent: EtOAc/Hexane =1/4) was carried out to isolate the desired product (57.7 mg, yield: 72%).

$^1$H NMR (400 MHz, $CDCl_3$) Isomer A δ 5.89 (s, 1H), 5.75 (d, J=2.54 Hz, 1H), 4.09 (t, J=6.09 Hz, 1H), 3.71 (t, J=1.76 Hz, 6H), 3.20-3.18 (m, 1H), 2.93-2.87 (m, 2H), 2.78-2.74 (m, 1H), 2.44-2.29 (m, 1H), 2.24-2.17 (m, 2H); Isomer B δ 5.87 (s, 1H), 5.73 (d, J=3.05 Hz, 1H), 4.09 (t, J=6.09 Hz, 1H), 3.71 (t, J=1.76 Hz, 1H), 3.20-3.18 (m, 1H), 2.93-2.87 (m, 2H), 2.78-2.74 (m, 1H), 2.44-2.29 (m, 1H), 2.24-2.17 (m, 2H)

Example 17

Preparation of 4-(4',4',5',5'-tetracyano-1'-cyclohexenyl)-2-azetidinone

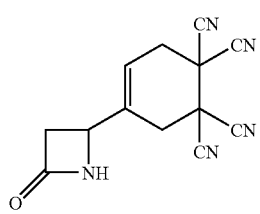

In a V-VIAL® vial, 3-[(1',3'-dien)-2'-yl]-2-azetidinone (36.9 mg, 0.3 mmol), tetracyano ethylene (76.85 mg, 0.6 mmol) and indium trichloride (2.78 mg, 0.015 mmol) were dissolved in 0.5 ml of a $CH_3CN$ solvent. The resulting solution was stirred for 24 hours at room temperature. Then, the reaction was terminated by adding a saturated aqueous $NH_4Cl$ solution (10 ml) to the solution. The mixture was extracted using $CH_2Cl_2$ (3 ×20 ml) and washed with a saturated aqueous NaCl solution (20 ml). The extracted organic layer was dried over anhydrous $MgSO_4$, and the residue was filtered off. After removing the solvent from the dried organic layer, column chromatography (eluent: EtOAc/Hexane =1/1) was carried out to isolate the desired product (64.1 mg, yield: 85%).

$^1$H NMR (400 MHz, $CDCl_3$) Isomer A δ 8.22 (s, 1H), 5.88 (s, 1H), 4.14 (s, 1H), 3.46 (d, J=18.33 Hz, 2H), 3.32 (d, J=18.23 Hz, 2H), 3.13 (d, J=5.29 Hz, 1H), 2.64 (s, 1H); Isomer B δ 8.22 (s, 1H), 5.88 (s, 1H), 4.14 (s, 1H), 3.46 (d, J=18.33 Hz, 2H), 3.32 (d, J=18.23 Hz, 2H), 3.09 (d, J=5.26 Hz, 1H), 2.60 (s, 1H)

Example 18

Preparation of 4-(4',5'-dimethoxycarbonyl-1',4'-cyclohexadien-1'-yl)-2-azetidinone

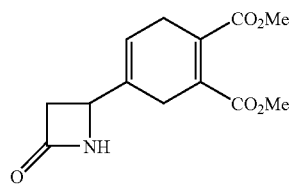

In a V-VIAL® vial, 3-[(1',3'-dien)-2'-yl]-2-azetidinone (36.9 mg, 0.3 mmol), dimethylacetylenedicarboxylate (85.27 mg, 0.6 mmol) and indium trichloride (2.78 mg, 0.015 mmol) were dissolved in 0.5 ml of a $CH_3CN$ solvent. The resulting solution was stirred for 24 hours at room temperature. Then, the reaction was terminated by adding a saturated aqueous $NH_4Cl$ solution (10 ml) to the solution. The mixture was extracted using $CH_2Cl_2$ (3 ×20 ml) and washed with a saturated aqueous NaCl solution (20 ml). The extracted organic layer was dried over anhydrous $MgSO_4$, and the residue was filtered off. After removing the solvent from the dried organic layer, column chromatography (eluent: EtOAc/Hexane =1/1) was carried out to isolate the desired product (66.0 mg, yield: 83%).

$^1$H NMR (400 MHz, $CDCl_3$) Isomer A δ 6.19 (s, 1H), 5.77 (s, 1H), 4.22 (dd, J=14.51, 14.26 Hz, 1H), 3.79 (s, 6H), 3.20 (dd, J=2.38, 5.27 Hz, 1H), 3.08 (m, 2H), 2.78 (d, J=1.99 Hz, 1H); Isomer B δ 6.19 (s, 1H), 5.77 (s, 1H), 4.22 (dd, J=14.51, 14.26 Hz, 1H), 3.79 (s, 6H), 3.16 (dd, J=2.34, 5.33 Hz, 1H), 3.08 (m, 2H), 2.75 (d, J=2.10 Hz, 1H)

Example 19

Preparation of 4-(4'-acetyl-1'-cyclohexenyl)-2-azetidinone

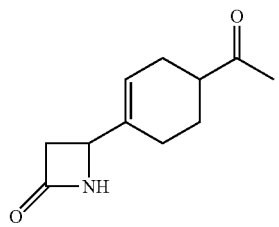

In a V-VIAL® vial, 3-[(1',3'-dien)-2'-yl]-2-azetidinone (36.9 mg, 0.3 mmol), methyl vinyl ketone (42.05 mg, 0.6 mmol) and indium trichloride (2.78 mg, 0.015 mmol) were dissolved in 0.5 ml of a $CH_3CN$ solvent. The resulting solution was stirred for 24 hours at room temperature. Then, the reaction was terminated by adding a saturated aqueous $NH_4Cl$ solution (10 ml) to the solution. The mixture was extracted using $CH_2Cl_2$ (3 ×20 ml) and washed with a saturated aqueous NaCl solution (20 ml). The extracted organic layer was dried over anhydrous MgSO$_4$, and the residue was filtered off. After removing the solvent from the dried organic layer, column chromatography (eluent: EtOAc/Hexane =1/1) was carried out to isolate the desired product (34.2 mg, yield: 59%).

$^1$H NMR (400 MHz, CDCl$_3$) δ 6.03 (s, 1H), 5.74 (s, 1H), 4.13-4.06 (m, 1H), 3.15-3.10 (m, 1H), 2.75-2.67 (m, 1H), 2.67-2.60 (m, 1H), 2.24-2.29 (m, 1H), 2.21-2.19 (m, 1H), 2.17-2.12 (m, 1H), 2.04-1.99 (m, 1H), 1.70-1.53 (m, 1H)

Example 20

Preparation of [3R(1'R,4S)]-3-[(1'-(tert-butyldimethylsilyloxy)ethyl)-4-[(4",4",5",5"-tetracyano-3",6"-dimethylene-1-cyclohexenyl]-2-azetidinone

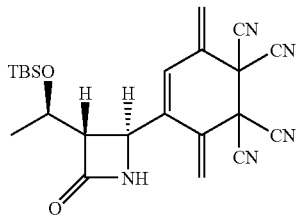

In a V-VIAL® vial, [3R(1'R,4S)]-3-[(1'-tert-butyldimethylsilyloxy)ethyl]-4-[(1",2",4",5"-hexatetraen)-3"-yl]-2-azetidinone (152.75 mg, 0.5 mmol) and teracyano ethylene (128.09 mg, 1.0 mmol) were dissolved in 0.8 ml of a benzene solvent. The resulting solution was stirred for 48 hours at 83° C. Then, the reaction was terminated by adding a saturated aqueous NH$_4$Cl solution (10 ml) to the solution. The mixture was extracted using CH$_2$Cl$_2$ (3 ×20 ml) and washed with a saturated aqueous NaCl solution (20 ml). The extracted organic layer was dried over anhydrous MgSO$_4$, and the residue was filtered off. After removing the solvent from the dried organic layer, column chromatography (eluent: EtOAc/Hexane =1/3) was carried out to isolate the desired product (192.9 mg, yield: 89%).

$^1$H NMR (400 MHz, CDCl$_3$) δ 6.78 (s, 1H), 6.34 (s, 1H), 6.30 (s, 1H), 6.17 (d, J=1.53 Hz, 1H), 5.98-5.96 (m, 2H), 4.72 (s, 1H), 4.35-4.27 (m, 1H), 2.97 (s, 1H), 1.22 (d, J=6.22 Hz, 3H), 0.91 (s, 9H), 0.12 (d, J=6.00 Hz, 6H)

According to the present invention, the compound represented by the chemical formula 1 has a novel structure which introduces an alkenyl group such as 1,3-dien-2-yl or 1,2,4,5-hexatetraen-3-yl to the C-4 position of β-lactam. Since the compound has the alkenyl group introduced to the C-4 position, it can be appropriately used in the Diels-Alder reaction as a diene reactant.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A 4-alkenyl-2-azetidinone derivative represented by the following chemical formula 1:

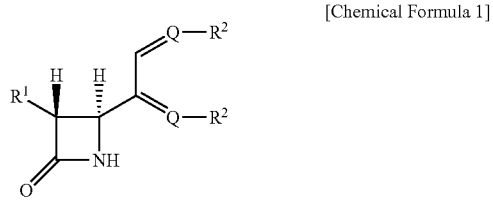

[Chemical Formula 1]

wherein, Q is CH or C=CH; R$^1$ is a hydrogen atom, a hydroxyalkyl or a protected hydroxyalkyl group having 1 to 6 carbon atoms; and R$^2$ is a hydrogen atom, an alkyl group having 1 to 6 carbon atoms or a phenyl group; provided that, a compound, wherein Q is CH, R$^1$ is a protected hydroxyalkyl group and R$^2$ is a hydrogen atom, is excluded.

2. A process for preparing a multicyclic compound represented by the following chemical formula 6a or 6b by subjecting the compound represented by the following chemical formula 1 and dienophile represented by the following chemical formula 5a or 5b to the Diels-Alder reaction:

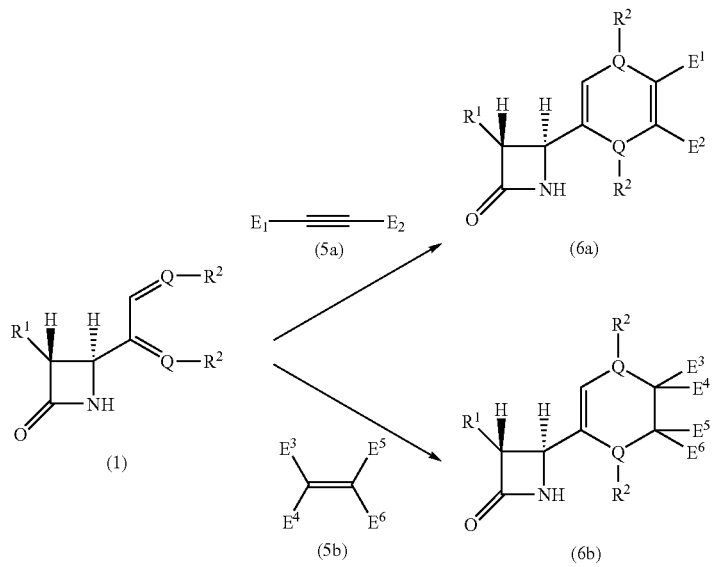

wherein, Q is CH or C=CH; $R^1$ is a hydrogen atom, a hydroxyalkyl or a protected hydroxyalkyl group having 1 to 6 carbon atoms and protected by tert-butyldimethysilyl group; and $R^2$ is a hydrogen atom, an alkyl group having 1 to 6 carbon atoms or a phenyl group; and $E^1$, $E^2$, $E^3$, $E^4$, $E^5$ and $E^6$ are respectively a hydrogen atom, a cyano group, C(=O)R, C(=O)OR or C(=O)NR$_2$, provided that R is a hydrogen atom or an alkyl group having 1 to 6 carbon atoms, and $E^3$, $E^4$, $E^5$ and $E^6$ is bonded with the adjacent group to form a cycle selected from dihydrofuran-2,5-dione, pyrrolidine-2,5-dione, pyrrolidine-2,5-dione substituted with 1-($C_1$-$C_6$ alkyl or phenyl), 2,3-dihydronaphthalene-1,4-dione, and naphthalene-1,4-diol.

3. The process according to claim 2, wherein the dienophile is selected from maleimide, N-ethylmaleimide, N-phenylmaleimide, dimethyl fumarate, dimethyl maleate, maleic anhydride, tetra(cyano)ethylene, dimethylacetylenedicarboxylate, methyl vinyl ketone, naphtoquinone, ethyl acrylate, and ethyl glyoxylate.

4. A multicyclic compound represented by the following chemical formula 6a:

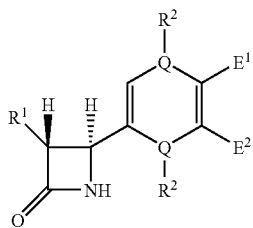

[Chemical Formula 6a]

wherein, Q is CH or C=CH; $R^1$ is a hydrogen atom, a hydroxyalkyl or a protected hydroxyalkyl group having 1 to 6 carbon atoms; and protected by tert-utyldimethysilyl group; and $R^2$ is a hydrogen atom, an alkyl group having 1 to 6 carbon atoms or a phenyl group; and $E^1$ and $E^2$ are respectively a hydrogen atom, a cyano group, C(=O)R, C(=O)OR or C(=O)NR$_2$, provided that R is a hydrogen atom or an alkyl group having 1 to 6 carbon atoms.

5. A multicyclic compound represented by the following chemical formula 6b:

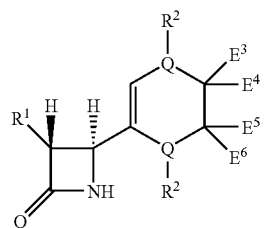

[Chemical Formula 6b]

wherein, Q is CH or C=CH; $R^1$ is a hydrogen atom, a hydroxyalkyl or a protected hydroxyalkyl group having 1 to 6 carbon atoms; and protected by tert-utyldimethysilyl group; and $R^2$ is a hydrogen atom, an alkyl group having 1 to 6 carbon atoms or a phenyl group; and $E^3$, $E^4$, $E^5$ and $E^6$ are respectively a hydrogen atom, a cyano group, C(=O)R, C(=O)OR or C(=O)NR$_2$, where R is a hydrogen atom or an alkyl group having 1 to 6 carbon atoms, and $E^3$, $E^4$, $E^5$ or $E^6$ are bonded with the adjacent group to form a cycle selected from pyrrolidine-2,5-dione, pyrrolidine-2,5-dione substituted with 1-($C_1$-$C_6$ alkyl or phenyl), 2,3naphthalene-1,4-diol.

* * * * *